US010072311B2

(12) United States Patent
Mayer

(10) Patent No.: US 10,072,311 B2
(45) Date of Patent: Sep. 11, 2018

(54) MICROORGANISMS FROM SOURDOUGH

(71) Applicant: LUDWIG STOCKER HOFPFISTEREI GmbH, München (DE)

(72) Inventor: Jürgen Mayer, München (DE)

(73) Assignee: Ludwig Stocker Hofpfisterei GmbH, Munich (DE)

(*) Notice: Subject to any disclaimer, the term of this patent is extended or adjusted under 35 U.S.C. 154(b) by 61 days.

(21) Appl. No.: 14/440,095

(22) PCT Filed: Nov. 7, 2013

(86) PCT No.: PCT/EP2013/073272
§ 371 (c)(1),
(2) Date: May 1, 2015

(87) PCT Pub. No.: WO2014/072408
PCT Pub. Date: May 15, 2014

(65) Prior Publication Data
US 2015/0292048 A1    Oct. 15, 2015

(30) Foreign Application Priority Data
Nov. 8, 2012  (EP) .................................... 12191813

(51) Int. Cl.
*A21D 8/04* (2006.01)
*C12P 7/62* (2006.01)
*C12R 1/225* (2006.01)
*A61K 35/747* (2015.01)
*A61K 8/99* (2017.01)
*A61Q 19/00* (2006.01)
*A61Q 19/08* (2006.01)

(52) U.S. Cl.
CPC ............... *C12R 1/225* (2013.01); *A21D 8/04* (2013.01); *A61K 8/99* (2013.01); *A61K 35/747* (2013.01); *A61Q 19/00* (2013.01); *A61Q 19/08* (2013.01); *A61K 2800/10* (2013.01)

(58) Field of Classification Search
None
See application file for complete search history.

(56) References Cited

U.S. PATENT DOCUMENTS

2010/0215738 A1* 8/2010 Ritter ................. A61K 31/7004
424/456

OTHER PUBLICATIONS

Herbert "How to Start a Sourdough Culture" The Guardian, Feb. 20, 2012.*

(Continued)

*Primary Examiner* — Robert J Yamasaki
*Assistant Examiner* — Charles Zoltan Constantine
(74) *Attorney, Agent, or Firm* — Rothwell, Figg, Ernst & Manbeck, P.C.

(57) ABSTRACT

The invention relates to novel *Lactobacillus* strains isolated from sourdough. Also encompassed is a composition comprising at least one of said *Lactobacillus* strains with optionally additional other microorganisms such as bacteria and/or yeasts. The invention further relates to the use of said *Lactobacillus* strains or compositions for the manufacture of human food products and food supplement products or animal feed products. Another aspect of the invention is the use of the *Lactobacillus* strains or the composition of *Lactobacillus* strains in human or veterinary medicine or in cosmetics.

25 Claims, 11 Drawing Sheets

(56) References Cited

OTHER PUBLICATIONS

Chavan "Sourdough Technology—Traditional Way for Wholesome Foods: A review" Comprehensive Reviews in Food Science and Food Safety vol. 10 2011.*

Korakli M: "sucrose metabolism and exopolysaccharide production in wheat and rye sourdoughs by Lactobacillus sanfranciscensis", Journal of Agricultural and Food Chemistry, American Chemical Society, US, vol. 49, No. 11, Jan. 2001 (Jan. 1, 2001), pp. 5194-5200, XP002188905, ISSN: 0021-8561, DOI: 10.1021/JF0102517, the whole document.

Susanne Kaditzky et al: "Performance of Lactobacillus sanfranciscensis TMW 1.392 and its levansucrase deletion mutant in wheat dough and comparison of their impact on bread quality", European Food Research and Technology ; Zeitschrift for Lebensmitteluntersuchung und-Forschung A, Springer, Berlin, DE, vol. 227, No. 2, Sep. 4, 2007 (Sep. 4, 2007), pp. 433-442, XP019621698, ISSN: 1438-2385 the whole document.

Korakli M et al: "Exopolysaccharide and kestose production by Lactobacillus sanfranciscensis LTH2590", Applied and Environmental Microbiology, American Society for Microbiology, US, vol. 69, No. 2, Apr. 1, 2003 (Apr. 1, 2003), pp. 2073-2079, XP002324282, ISSM: 0099-22400, DOI: 10.1128/AEM.69.4.2073-2079.2003 the whole document.

Rudi F Vogel et al: "Genomic analysis reveals Lactobacillus sanfranciscensis as stable element in traditional sourdoughs", Microbial Cell Factories, Biomed Central, London, NL, vol. 10, No. Suppl 1, Aug. 30, 2011 (Aug. 30, 2011), p. S6, XP021105393, ISSN: 1475-2859, DOI: 10.1186/1475-2859-10-S1-S6 the whole document.

De Angelis et al: "Molecular and functional characterization of Lactobacillus sanfranciscensis strains isolated from sourdoughs", International Journal of Food Microbiology, Elsevier Science Publishers, Amsterdam, NL, vol. 114, No. 1, Feb. 3, 2007 (Feb. 3, 2007), pp. 69-82, XP005871972, ISSN: 0168-1605, DOI: 10.1016/JAHOODMICRO.2006.10.036 the whole document.

International Search Report cited in PCT/EP2013/073272 dated Feb. 3, 2014.

* cited by examiner

MICROORGANISMS FROM SOURDOUGH

CROSS REFERENCE TO RELATED APPLICATION

This application is a 35 U.S.C. 371 National Phase Entry Application from PCT/EP2013/073272, filed Nov. 7, 2013, which claims the benefit of EP Patent Application No. 12191813.0 filed on Nov. 8, 2012, the disclosure of which is incorporated herein in its entirety by reference.

The invention relates to novel *Lactobacillus* strains isolated from sourdough. Also encompassed is a composition comprising at least one of said *Lactobacillus* strains with optionally additional other microorganisms such as bacteria and/or yeasts. The invention further relates to the use of said *Lactobacillus* strains or compositions for the manufacture of human food products and food supplement products or animal feed products. Another aspect of the invention is the use of the *Lactobacillus* strains or the composition of *Lactobacillus* strains in human or veterinary medicine, or in cosmetics.

The expression "Lactic acid bacterium" or "*Lactobacillus*" designates an organism of a group of Gram-positive, catalase negative, non-motile, microaerophilic or anaerobic bacteria which ferment sugars, thereby producing acids including lactic acid as a major product as well as acetic acid, formic acid and/or propionic acid. The industrially most useful lactic acid bacteria are found among *Lactobacillus* species, *Lactococcus* species, *Oenococcus* species, *Streptococcus* species, *Weissella* species, *Enterococcus* species, *Leuconostoc* species and *Pediococcus* species.

Lactic acid bacteria are microbes producing lactic acid, which inhibits the growth of pathogenic and harmful bacteria, by lactic acid fermentation. They are also involved in the regulation of the intestinal microflora by the production of lactic acid and specific antibacterial substances. Furthermore, they are involved in immune modulating processes concerning inflammatory aspects associated with age-related diseases such as neuronal diseases, e.g. Parkinson, Alzheimer or Age-related macular degeneration (AMD) and vascular diseases, e.g. atherosclerosis or stroke and others.

Lactic acid bacteria are used extensively for industrial fermentation processes in the industry, both in the manufacture of food, feed and pharmaceutical products, including manufacturing of dairy products such as cheese, yoghurt, and butter. They are also essential for the production of certain food products such as in the production of fermented vegetables, cereals, bread and meat. Additionally, they are increasingly used as pro-biotics for human and animals where it can be given as pure cultures or added or incorporated in the food or feed or even added to sweets.

Cultures of lactic acid bacteria are e.g. used in the manufacturing of sourdough-bread, a process that involves the inoculation of a mixture of flour and water followed by fermentation, sometimes for several days, freshing with flour and water and finally mixing into the bread dough which is kneaded and allowed to rise slowly before baking. In comparison with bread types produced with cultivated yeasts, it usually has a mildly sour taste because of the lactic acid produced by the *Lactobacilli*. The pH value in the dough is stepwise decreased to 4.0-4.3 by the acidification. The underlying processes thereby are responsible for the formation of odorous substances and flavouring substances which are characteristic for the bread.

Especially in a multistep sourdough leavening process, *Lactobacilli* and yeast species are involved, responsible for the characteristic taste and flavour of the sourdough bread.

Another striking advantage of the sourdough leavening process are the long shelf-life, anti-mold and anti-bacterial effect, as well as increased organoleptic properties of the sourdough bread compared to non-sourdough bread.

In particular, *Lactobacillus fermentum*, *Lactobacillus brevis*, *Lactobacillus kefiri*, and strains of *Lactobacillus sanfranciscensis* are known to metabolise hexose sugars via the Embden-Meyerhof-Parnas (EMP) pathway to produce lactic acid, acetic acid and $CO_2$. Pentose sugars are metabolised via the phosphogluconate pathway to lactic and acetic acids.

*Lactobacillus sanfranciscensis* was named for its discovery in San Francisco sourdough starters, although it is not endemic in San Francisco. The San Francisco sourdough is a type I sourdough, such type I sourdoughs have a pH range of 3.8-4.8 and are fermented in a room temperature range of 20-30° C. (Golden, D. et al, Modern Food Microbiology, 2005, Springer Verlag, p. 179). They are further characterised by continuous daily refreshments with flour of the starter culture to keep the microorganisms in an active state. So-called type II sourdoughs contain additionally *Saccharomyces cerevisiae* to leaven the dough. Those sourdoughs have a pH of less than 3.5 and are fermented within a temperature range of 30-50° C. for several days without feedings, which reduces the flora's activity (Sadeghi, A., Biotechnology, 2008, 7, 413 and Ercolini, D. and Cocolin, L., Molecular Techniques in the Microbial Ecology of Fermented Foods, 2008, Springer Verlag, p. 119). The type II sourdoughs are often used to acidify the dough and are semi-fluid silo preparations. Type III sourdoughs are dried preparations containing *Lactobacilli* resistant to freeze-drying. They require as well as type II sourdoughs the addition of *Saccharomyces cerevisia* as leavening agent. During the fermentation, lactic acid is produced by a biological process by which sugars such as glucose, fructose, and sucrose are converted into cellular energy and into metabolic lactate under anaerobic conditions (Fermented Fruits and Vegetables—A Global Perspective, 1998, United Nations).

Various *Lactobacillus* strains may differ from each other in terms of their properties, such as fermentation rate or metabolite production.

Especially for industrial application, the performance of various *Lactobacillus* strains for the production of fermented products is a significant feature which has to be optimized in order to gain better fermentation results and/or improvements in the bouquet of the flavouring and odorous substances.

The underlying problem of the present invention is to provide novel lactic acid bacteria which are particularly suitable for the manufacture of human food, animal feed and therapeutic purposes in human and veterinary medicine, as well as the application in cosmetics.

During an analysis of different sourdough samples, nine novel *Lactobacillus* strains have been identified. These strains have been deposited at the Leibnitz-Institut DSM—Deutsche Sammlung von Mikroorganismen und Zellkulturen GmbH (Braunschweig, Germany), according to the Budapest Treaty. The novel *Lactobacillus* strains have the following accession numbers and deposition dates: DSM 23090 (2012 Jun. 21), DSM 23091 (2012 Jun. 21), DSM 23200 (2012 Jun. 21), DSM 23092 (2012 Jun. 21), DSM 23093 (2012 Jun. 21), DSM 23201 (2012 Jun. 21), DSM 26024 (2012 Jun. 4), DSM 23174 (2012 Jun. 21), DSM 23121 (2012 Jun. 21). The new bacteria strains have been identified as *Lactobacillus sanfranciscensis* and *Lactobacillus rossiae*, respectively. The *Lactobacillus sanfranciscensis* strains have a 97.5-99.2% identity of the 16S rRNA compared to the prototype strain of *Lactobacillus sanfrancis-*

*censis* (Table 3). The deposited strains are very well suited for the production of fermented products for human or animal use. The deposited strains are particularly suitable for use in the manufacture of sourdough, more particularly for use in multistep sourdough leavening processes. Advantageously the deposited strains contribute in providing excellent flavours in combination with a well-balanced ratio of metabolites beneficial for human and animal health (Table 4 and FIGS. 1-3).

The present invention provides a *Lactobacillus* strain selected from any one of the strains DSM 23090, DSM 23091, DSM 23200, DSM 23092, DSM 23093, DSM 23201, DSM 26024, DSM 23174 and DSM 23121 or a strain cultivated therefrom. Preferably a *Lactobacillus* strain selected from any one of the strains DSM 23090, DSM 23091, DSM 23200, DSM 23092, DSM 23093, DSM 23201, DSM 26024, DSM 23174 and DSM 23121, is provided.

The term "a strain cultivated therefrom" as used herein means offspring strains derived by cultivation of the original strain.

In some embodiments, the invention relates to combinations of at least 2, 3, 4, 5, 6, 7, 8, 9 strains.

The strains may be provided as a liquid or solid preparation, e.g. as a liquid cell suspension or as a frozen, spray-dried or freeze-dried preparation.

The strains of the invention are capable of producing metabolites selected from mannite, lactate, acetate, and combinations thereof. The metabolites may be produced in concentrations of about 5-70 mmol mannite/kg culture medium, about 10-110 mmol lactate/kg culture medium and about 5-50 mmol acetate/kg culture medium.

In a preferred embodiment, a combination of several *Lactobacillus* strains of the invention or strains cultivated therefrom is characterized in that it produces the metabolites mannite, lactate and acetate, in particular in concentrations of about 5-70 mmol mannite/kg culture medium, about 10-110 mmol lactate/kg culture medium and about 5-50 mmol acetate/kg culture medium. In a more preferred embodiment, the metabolites produced by the bacteria may be in concentrations of about 40-60 mmol mannite/kg culture medium, about 50-100 mmol lactate/kg culture medium and about 20-42 mmol acetate/kg culture medium. The culture medium may be any suitable culture medium, particularly dough, more particularly sourdough.

The strains of the invention show a significantly different metabolite profile especially with regard to the produced amino acid concentrations compared to the *Lactobacillus sanfranciscensis* type strain (DSM 20451). A low amount of amino acids, in particular leucine, isoleucine and valine, is preferred for bread baking to reduce the amount of bitter compounds produced during the baking process. This leads to a reduced amount of salt (NaCl) which has to be added to the dough to reduce the bitter taste.

The strains of the invention are capable of producing amino acids selected from arginine, phenylalanine, valine, leucine, isoleucine, histidine and combinations thereof. This amino acids may be produced in concentrations of at least 2.0 mM arginine, preferably of about 2.0-3.0 mM arginine, at least 2.0 mM phenylalanine, preferably of about 2.0-2.6 mM phenylalanine, at least 5 mM valine, preferably of about 5-12 mM valine, at least 10 mM leucine, preferably of about 10-24 mM leucine, at least 3 mM isoleucine, preferably of about 3-7 mM isoleucine, and at least 1 mM histidine, preferably of about 1-1.5 mM histidine.

In a preferred embodiment the *Lactobacillus* strains of the invention are characterized in that they produce at least 5 mM valine, preferably of about 5-12 mM valine, at least 10 mM leucine, preferably of about 10-24 mM leucine, and at least 3 mM isoleucine, preferably of about 3-7 mM isoleucine.

The strains of the invention are also capable of producing acetylcholine (ACH) in concentrations of at least 0.02 mM ACH, preferably of about 0.02-0.25 mM ACH.

The presence of acetylcholine leads to improved pharmaceutical properties (cf. co-pending application EP 13 153 996.7) and assists the digestion of food by stimulating the stomach and intestinal motility as well as intestinal secretion.

In a preferred embodiment a combination of several *Lactobacillus* strains of the invention is characterized in that it produces the amino acids arginine, phenylalanine, valine, leucine, isoleucine and histidine, in particular in concentrations of about 2.0-3.0 mM arginine, about 2.0-2.6 mM phenylalanine, about 5-12 mM valine, about 10-24 mM leucine, about 3-7 mM isoleucine and about 0.1-1.5 mM histidine. More preferably the combination is characterised in that it produces at least 5 mM valine, preferably of about 5-12 mM valine, at least 10 mM leucine, preferably of about 10-24 mM leucine and at least 3 mM isoleucine, preferably of about 3-7 mM isoleucine. The combination is further characterized in that it produces acetylcholine, in particular in concentrations of about 0.1-0.25 mM acetylcholine. The culture medium may be any suitable culture medium, particularly dough, more particularly sourdough.

Another embodiment of the invention is a composition comprising at least one *Lactobacillus* strain selected from the group of DSM 23090, DSM 23091, DSM 23200, DSM 23092, DSM 23093, DSM 23201, DSM 26024, DSM 23174, and DSM 23121 or a strain cultivated therefrom, and a nutritionally or pharmaceutically acceptable carrier. In a preferred embodiment, the composition can contain 2, 3, 4, 5, 6, 7, 8, and/or 9 strains of the *Lactobacilli* of the invention. In the most preferred embodiment, the composition contains at least 5 of the strains of the invention.

The composition of the invention may further comprise at least one further microorganism. The further microorganism can be a bacterium and/or a yeast. Said bacterium or yeast is preferably a nutritionally or pharmaceutically compatible strain which does not have pathological properties known to be harmful for human or animals. In a preferred embodiment, the further bacterium and/or yeast is suitable for production of animal and/or human food and/or beverages. In another preferred embodiment, the further bacterium and/or yeast is suitable to ferment a substrate and thereby providing beneficial metabolites for human or animal health. The further bacterium may be selected from a group consisting of *Lactobacillus sanfranciscensis* strains, *Lactobacillus rossiae* strains, *Lactobacillus plantarum* strains, *Lactobacillus brevis* strains, *Lactobacillus amyolyticus* strains, *Lactobacillus amylovarus* strains, *Lactobacillus delbrückii* strains, *Lactobacillus pontis* strains, *Lactobacillus acidophilus* strains, *Lactobacillus lactis* strains and/or *Gluconobacter oxydans* strains. The further yeast strain is selected from a group consisting of *Candida humilis* strains, *Candida milleri* strains, *Candida krusei* strains, *Saccharomyces exiguus* strains, *Saccharomyces barnetti* strains, *Saccharomyces cerevisiae* strains and/or *Saccharomyces minor* strains. In a more preferred embodiment, the yeast is a *Saccharomyces barnetti* strain.

The composition may contain the microorganisms of the invention in an amount of about 0.1 to about 99% by weight, preferably from about 2 to about 20% by weight, even more preferably from about 4 to about 10% by weight, based on the total weight of the composition. Further, the composition may contain the microorganisms of the invention in an amount of about 10 to $10^{12}$ cfu/g (colony forming units/g), preferably of about $10^4$ to $0.5 \times 10^{12}$ cfu/g, more preferably of about $10^7$ to $10^{11}$ cfu/g based on the total weight of the composition.

The composition may be a liquid or solid composition (e.g. lyophilized, pulverized or powdered).

The composition may further comprise a culture medium suitable for cultivation of bacteria and/or yeasts, in particular a culture broth, a concentrate of the culture broth and/or a dry matter of the culture broth. The culture medium can be any medium known in the art for the cultivation of microorganisms, in particular *Lactobacilli*. The culture medium can be a solid culture medium like an agar-based growth medium, a dough, in particular sourdough, or any other solid media suitable for the cultivation of microorganisms, in particular *Lactobacilli*. The culture medium may also be a liquid culture medium wherein the bacteria are suspended in a culture broth or a liquid nutrient medium.

The culture medium may comprise ingredients suitable for the cultivation of *Lactobacilli* strains, such as carbon sources, e.g. glucose or maltose, nitrogen sources, e.g. peptone or meat extract, phosphorus sources, e.g. potassium dihydrogenphosphate, essential metal salts for bacterial growth and optionally growth-promoting substances like amino acids and/or vitamins. The culture medium preferably has a pH in the acidic range, in particular below pH 6. In some embodiments, the culture medium comprises the amino acid D-alanine since the antiinflammatory potential of *Lactobacilli* may be increased by an induction of a high IL-10/IL-12-ratio depending on the percentage of D-alanine (D-Ala) within the teichoic acid of their cell walls. A content of D-Ala of 1% in a mutant of *Lactobacillus plantarum* in comparison to 41% in the wild type reduced the induced IL-12/IL-10 ratio of Interleukin-induction in exposed Monocytes from 122 down to 3 (Gragnette et al., Proc. Natl. Acad. Sci. USA 102 (2005), 10321; Foligne et al., J. Gastroenterol. 13 (2007), 236).

In a preferred embodiment, the culture medium comprises at least water, yeast and flour and/or malt of a cereal and/or a pseudocereal such as wheat, triticale, rye, barley, spelt, einkorn wheat, oat, buckwheat, kamut, emmer, millet, rice, corn, sorghum, amaranth, quinoa, hemp, lupine or combinations thereof. Optionally, salt or spice or spice mixtures can be added to the culture medium prior or after fermentation of the medium.

A composition for medical or nutritional use may be in solid or liquid dosage forms, such as for example tablets, coated tablets, capsules, solutions, suspensions, emulsions, pellets, syrups and so on and are prepared in the usual manner by mixing the active ingredient with excipients and/or carriers such as e.g. natural mineral flours (kaolin, talc) or synthetic mineral flours (e.g. silicates), optionally adding adjuvants (e.g. glycol) and/or dispersing agents (e.g. methyl cellulose).

Optionally, the composition can also contain a prebiotic. As used herein, a "prebiotic composition" is an at least non-digestible food ingredient that beneficially affects the host by selectively stimulating the growth, activity or both of one of a limited number of species of microorganisms already resident in the colon. The prebiotic is preferably a non-digestible oligosaccharide such as fructo-oligosaccharides, galacto-oligosaccharides, lactolose, xylo-oligosaccharides, ismalto-oligosaccharides, soy bean oligosaccharides, gentio-oligosaccharides, gluco-oligosaccharides, fructans, lactosucrose, short-chain fructo-oligosaccharides, and mixtures thereof.

Another preferred embodiment of the invention is a composition wherein the composition is a starter culture and/or fermentation starter for the manufacture of fermented products such as beverages, cheese, yoghurt or bread.

In another preferred embodiment the microorganisms can be applied to an edible material, preferably food—or feed product, in particular oat flakes or yoghurt.

A further aspect of the present invention refers to the use of the *Lactobacillus* strains or a strain cultivated therefrom or of the composition described above for the manufacture of human food products and food supplement products or animal feed products.

As used herein, the term "fermented" refers to a product made by adding at least one microorganism such as lactic acid bacteria or yeasts to perform a fermentation by the microorganisms. Specifically, the term refers to foods and feeds made by adding the fermentation starter to food or feed bases which are then incubated. A fermentation starter comprises, as an active ingredient, at least one strain selected from the group of DSM 23090, DSM 23091, DSM 23200, DSM 23092, DSM 23093, DSM 23201, DSM 26024, DSM 23174, and DSM 23121 or a strain cultivated therefrom, a culture broth of the strain, and/or a concentrate of the culture broth, and/or a dry matter of the culture broth. In another embodiment, the fermentation starter comprises a microbial strain of the invention applied to a carrier acceptable in food technology or pharmaceutical sciences, such as silicon dioxide or diatomaceous earth.

As used herein, the term "food product" means foods of plantal or animal origin which provide the required nutrients to the organism. The food product may be a milk-based product, a vegetable product, a meat product, a fruit juice, a wine and a bakery product or other unpasteurised open-fermented foods, preferably such as alcoholic and non-alcoholic beverages, breads, kimchi, salted-fermented sea foods, soy bean paste, cheese, yoghurt, wort and the like. More preferably, the food product is a sourdough or a beverage, in particular sourdough bread.

A food supplement product as used herein is a preparation intended to supplement the diet and provide nutrients, such as vitamins, minerals, fibres, fatty acids, amino acids and/or enzymes, that may be missing or may not be consumed in sufficient quantities in a persons diet. Other supplement may contain important regulatory components for human health such as β-glucans from yeast or multiple polyphenols from sources such as green tea, fermented tea, red wine extracts, grape seed extracts, cranberry or aronia extracts or juice etc. Further typical food supplement products are fermented concentrates.

The term "feed product" as used herein means substances or food products, as well as additives, which, depending on their level of processing, are intended for oral feeding of animals, e.g. cattle, pigs or deer.

Useful feed products starting materials include any material which is conventionally subjected to lactic acid bacterial fermentation step such as silage, e.g. grass, cereal material, peas, alfalfa- or sugar-beat leaf where the bacterial culture is inoculated in a feed crop to be ensiled in order to obtain preservation hereof, or in protein-rich animal waste products such as slaughtering offal and fish offal, also with aims of preserving this offal for animal feeding purposes.

The invention, however, also refers to the use of *Lactobacillus* strains or compositions as described above in human or veterinary medicine, or in cosmetics.

A preferred medical use, in this respect, is to provide lactic acid bacteria strains being capable of modulating the immune response and thus being capable of regulating an inflammatory syndrome. While not wishing to be bound by theory, the inventors assume that the lactic acid bacteria strains disclosed herein are capable of balancing the TH1- and/or TH2-immune response versus the regulatory Tcell (TH17)-intervention to obtain a neutralizing equilibrium minimizing noxious and adverse symptoms, whereby T-helper cells are modulated in their activities so that allergic (TH2) or inflammatory reactions (TH1) are suppressed by emphasizing the IL-10 release.

The immune modulating properties of the lactic acid bacteria strains of the present invention are also shown in Example 5. Sourdough containing the claimed bacterial strains reduces the activity of defense cells, due to an antioxidative effect caused by the property of certain bacterial metabolites to neutralize reactive oxygen species (ROS). Under certain conditions the sourdough is also able to stimulate the immune system by enhancing the activity of defense cells.

Sourdough bread made from sourdough containing the bacterial strains according to the invention exhibits immune modulating properties. The immune modulating activity in the crumb is not getting lost during the baking process and is due to the bacterial cell walls which stimulate the immune system. The anti-oxidative activity is mainly localized in the bread crust.

A preferred cosmetical use in this respect is to provide lactic acid bacteria being capable of modulating the ageing process of the skin and to alleviate the consequences of ageing. While not wishing to be bound by theory, the metabolites produced by the lactic acid bacteria strains according to the invention activate the sirtuin proteins and thereby alleviate the skin degradation caused by oxidative stress. Especially the combination of amino acids, antioxidative polyphenols and the lactic acid milieu provided by the bacterial strains according to the invention prevents the oxidative degradation of supporting elements of the connective tissue, e.g. the depolymerisation of hyaluronic acid. In particular the amino acids act as scavengers for reactive oxygen species (ROS) such as hypochlorous acid under formation of the corresponding chloramines, which results in a detoxification of the ROS. Furthermore, said combination leads to an improvement of the hydrostatic tension of the skin and to an immunomodulatory reduction of allergic dispositions. As a result of those effects a smoothing of the skin can be achieved.

In a further preferred embodiment, the composition is incorporated into skin care or cosmetic products.

Another aspect of the present invention is the use of a *Lactobacillus* strain selected from the group of DSM 23090, DSM 23091, DSM 23200, DSM 23092, DSM 23093, DSM 23201, DSM 26024, DSM 23174 and DSM 23121 for the cultivation of a further *Lactobacillus* strain therefrom.

Figure 1:
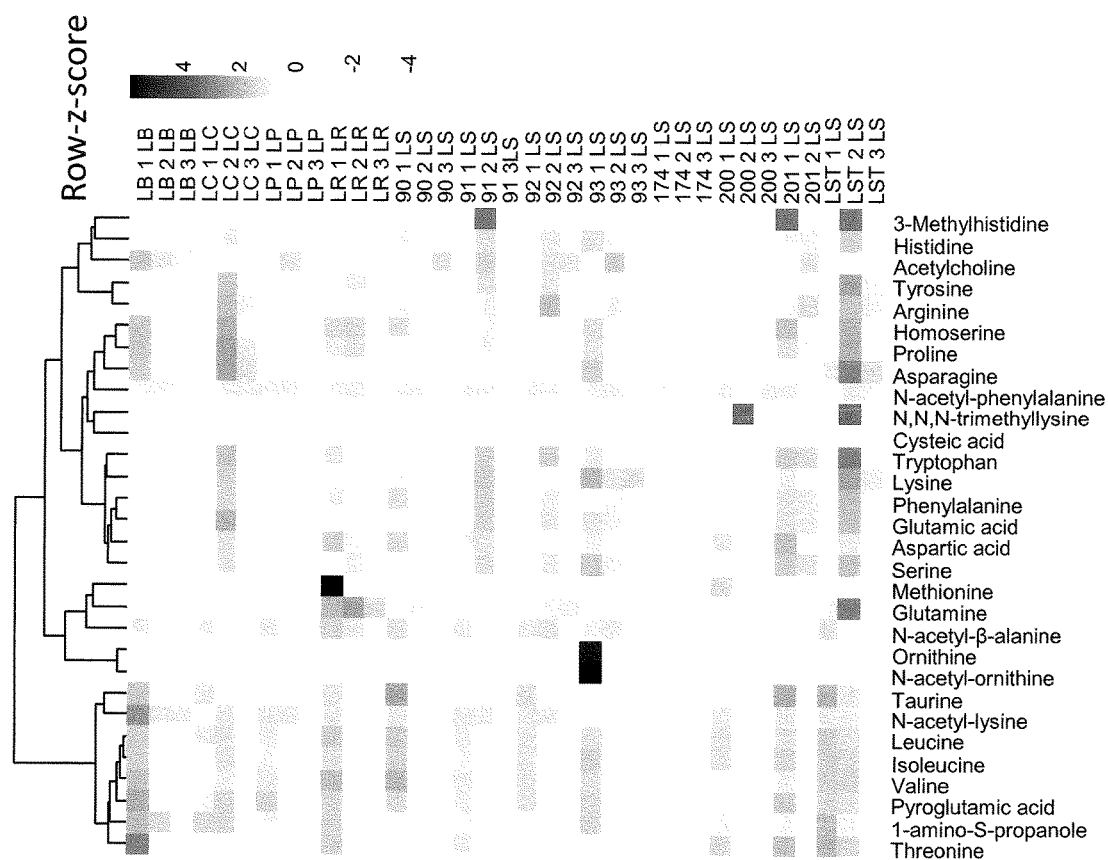
FIG. 1: Heatmap of the relative metabolite concentrations in MRS broth after 24 hour inoculation with *Lactobacillus rossiae* DSM 26024 (LR), *Lactobacillus sanfranciscensis* strain DSM 23090 (90 LS), *Lactobacillus sanfranciscensis* strain DSM 23091 (91 LS), *Lactobacillus sanfranciscensis* strain DSM 23092 (92 LS), *Lactobacillus sanfranciscensis* strain DSM 23093 (93 LS), *Lactobacillus sanfranciscensis* strain DSM 23174 (174 LS), *Lactobacillus sanfranciscensis* strain DSM 23200 (200 LS), *Lactobacillus sanfranciscensis* strain DSM 23201 (201 LS) and *Lactobacillus sanfranciscensis* type strain DSM 20451 (LST).

Further, the invention shall be explained in more detail by the following Examples.

EXAMPLE 1

1. Analysis of Sourdough Samples 4 sourdough samples were analysed which were each frozen and cooled, respectively (Table 1).

TABLE 1

| Samples | | |
| --- | --- | --- |
| Numbering | Dough | Fermentation |
| 1 | Whole grain starter dough | fermented |
| 2 | Whole grain finished dough | young |
| 3 | Starter dough | fermented |
| 4 | Finished dough | young |

Determination of pH Values and Counts of Bacteria and Yeasts.

The pH values of the doughs were determined with a glass electrode. In order to determine the cell counts, the cooled and frozen doughs were serially diluted in buffered peptone water and plated on modified MRS agar. Modified MRS-agar for determining the bacteria counts contained 100 mg/l cycloheximide for inhibition of yeast growth. These were incubated aerobically for 48 hours at 30° C. Modified MRS-agar for determining the yeast counts contained 100 mg/l chloramphenicol. These plates were incubated aerobically for 48 hours at 30° C.

Identification and Characterization of Bacteria.

In order to identify bacteria strains present in the sample, morphologically differing isolates were picked from the plates of the highest dilution stage (germ numbers in between 15 and 150) and spread out. Single colonies were incubated in liquid modified MRS buffer for 24 hours at 30° C. DNA was isolated from a total of 77 colonies with the Dneasy Blood & Tissue Kit (Quiagen, Missiauga, Canada) from cooled and frozen doughs.

Clonal isolates were eliminated by way of RepPCR with two primer pairs (Box2AR und GTG5). For taxonomic identification of the isolates, the 16S rRNA gene was sequenced from 25 isolates. The 16S rRNA genes were amplified with PCR (Primer 616V, 630R). PCR products (about 1500 base pairs) were cleaned up with the Qiagen PCR Purification Kit and sequenced by Macrogen (Rockville, Md., USA). The sequences were compared to the strains in the data base Project 9 (http://rdp.cme.msu.edu/).

Analysis of Metabolite Concentration.

The concentrations of maltose, mannite, lactate, glycerol, acetate and ethanol were determined by HPLC. For sample preparation, the doughs were diluted 1:1 with 7% of perchloric acid and incubated over night at 4° C. The supernatant was directly analysed. Separation was conducted on an Aminex HP87X column (Biorad), elution was carried out with 5 mM $H_2SO_4$ at 0.4 mL $min^{-1}$ and 70° C. The quantification was based on refractive index (RI) detection and external standard substances.

Results

Germ Numbers and pH Values.

Lower pH values and higher amounts of bacteria and yeasts in the cooled doughs point to a post-fermentation during delivery. Lower numbers of yeasts in the frozen doughs were due to partial mortification of the yeasts during the freezing. The number of bacteria in the cooled doughs was similarly in between log 8.3 and 8.9 germ-forming units (GFU) per g (Table 2). An exception to this was the frozen whole grain starter with higher germ numbers in the frozen dough than in the cooled one.

TABLE 2 pH values and numbers of germs in the delivered doughs

| Dough number | Status of delivery | pH | Number of bacterial germs log (GFU/g) | Number of yeast germs log (GFU/g) |
|---|---|---|---|---|
| 1 | cooled | 3.83 | 8.82 ± 0.12 | 7.14 ± 0.24 |
| 2 | cooled | 3.81 | 8.49 ± 0.17 | 6.82 ± 0.2 |
| 3 | cooled | 3.67 | 8.73 ± 0.19 | 6.64 ± 0.11 |
| 4 | cooled | 3.73 | 8.20 ± 0.13 | 6.83 ± 0.01 |
| 1 | frozen | 4.04 | 9.41 ± 0.26 | 5.48 ± 0.36 |
| 2 | frozen | 4.98 | 8.07 ± 0.25 | 4.22 ± 0.13 |
| 3 | frozen | 4.05 | 7.63 ± 0.09 | 4.23 ± 0.22 |
| 4 | frozen | 5.1 | 7.33 ± 0.77 | 3.7 |

Identification of Isolated Strains.

25 isolates of 10 strains distinguishable by random amplified polymorphic DNA (RAPD) typing were selected for sequencing. 20 isolates were identified as *Lactobacillus sanfranciscensis* which were allocated to different strains on the basis of RAPD pattern d8 (Table 3). Several strains were isolated in the cooled and frozen samples of the same doughs. Several strains could be isolated from the whole grain dough as well as the sourdough (strain No. 3, 4, 5, and 6).

Five isolates from the frozen doughs were identified to be *Staphylococcus* spp.

The isolated *Lactobacillus sanfranciscensis* strains were deposited at the Deutsche Sammlung von Mikroorganismen und Zellkulturen GmbH. The DSM-number is indicated in Table 3.

TABLE 3

Taxonomic identification of isolates of the sourdoughs.

| Isolate No. | Dough (number of isolates) | strain | Sequence identity of the 16S rRNS sequence to type strain [%] | DSM number |
|---|---|---|---|---|
| 1 | 1(1) | L. sanfranciscensis | 99.1 | 23090 |
| 2 | 1(1) | Staphylococcus pasteuri | 99.1 | — |
| 3 | 1(1), 2(2), 3(1) | L. sanfranciscensis | 98.6 | 23091 |
| 4 | 1(1), 3(1), 4(2) | L. sanfranciscensis | 99.2 | 23200 |
| 5 | 1(1), 3(2), 4(3) | L. sanfranciscensis | 98.8 | 23092 |
| 7 | 2(1) | L. sanfranciscensis | 98.9 | 23093 |
| 9 | 2(1), 3(1) | L. sanfranciscensis | 97.5 | 23201 |
| 15 | 3(2) | L. sanfranciscensis | 98.3 | 23174 |
| 17 | 4 | L. sanfranciscensis | 98.3 | 23121 |
| 21 | 4(3) | Staphylococcus warneri | 98.3 | — |

Quantitative Analysis of Metabolite Composition.

Taxonomic characterisation of the sourdough flora was supported by metabolite analysis. The presence of mannite and acetate in the sourdoughs confirmed the dominance of the microflora by the heterofermentative leading bacterium *Lactobacillus sanfranciscensis* (Table 4). Glycerol and ethanol could be attributed to the metabolism of yeasts. Post-fermentation which took place during delivery could also be observed in the analysis of the metabolites. Lactate, glycerol and ethanol were present in much higher concentrations in the cooled doughs. Accordingly, maltose and high glucose concentrations could only be detected in frozen doughs. In the frozen doughs, the fermented whole grain starter exhibited the highest amounts of lactate and acetate, probably because of the higher buffer capacity of whole grain flour as compared to wheat flour.

TABLE 4

Metabolite concentration in mmol per kg sourdough

| Dough | delivery | maltose | glucose | mannite | lactate | glycerol | acetate | ethanol |
|---|---|---|---|---|---|---|---|---|
| 1 | cooled | 0 | 3.6 ± 0.8 | 47.7 ± 8.2 | 97.5 ± 11.6 | 25.9 ± 4.6 | 40.3 ± 3.2 | 246.4 ± 23 |
| 2 | cooled | 0 | 1.3 ± 1.0 | 47.3 ± 5.5 | 87.7 ± 12.5 | 24.9 ± 2.1 | 34.3 ± 1.7 | 240.3 ± 16 |
| 3 | cooled | 0 | 3.3 ± 0.6 | 57.6 ± 7.9 | 80.0 ± 6.9 | 28.0 ± 1.2 | 34.8 ± 3.9 | 298.2 ± 26 |
| 4 | cooled | 0 | 3.3 ± 0.7 | 47.9 ± 9.3 | 63.6 ± 19.3 | 30.5 ± 4.7 | 30.9 ± 6.6 | 243.9 ± 60 |
| 1 | frozen | 0 | 4.5 ± 1.8 | 35.5 ± 2.8 | 68.2 ± 6.2 | 25.0 ± 3.4 | 29.3 ± 4.6 | 175.3 ± 20 |
| 2 | frozen | 0 | 20.2 ± 3.5 | 10.5 ± 1.9 | 27.1 ± 2.5 | 10.9 ± 5.0 | 14.2 ± 1.7 | 71.1 ± 15 |

TABLE 4-continued

Metabolite concentration in mmol per kg sourdough

| Dough | delivery | maltose | glucose | mannite | lactate | glycerol | acetate | ethanol |
|---|---|---|---|---|---|---|---|---|
| 3 | frozen | 1.7 ± 0.7 | 14.9 ± 1.8 | 33.1 ± 7.1 | 50.8 ± 6.7 | 17.1 ± 3.7 | 20.6 ± 4.2 | 107.4 ± 23 |
| 4 | frozen | 2.4 ± 0.3 | 15.0 ± 1.1 | 6.2 ± 0.4 | 12.6 ± 0.6 | 4.2 ± 0.4 | 5.1 ± 1.0 | 30.5 ± 8 |

3. Summary

The two tested doughs (whole grain dough samples 1 and 2 and dough samples 3 and 4) exhibited significant differences with regard to the composition of the microflora. Several different strains of *Lactobacillus sanfranciscensis* were identified.

The heterofermentative metabolism of *Lactobacillus sanfranciscensis* explained the formation of lactate, mannite, and acetate. Metabolism of sourdough yeasts led to the formation of glycerol and ethanol.

EXAMPLE 2

Isolation of *Lactobacillus rossiae* Strain DSM26024

Under similar conditions as described in Example 1, the *Lactobacillus rossiae* strain DSM26024 has been isolated on MRS plates (1.5% agar, 0.15% L-cystein, pH 5.4) from sourdough and identified by colony morphology and 16S DNA sequencing.

EXAMPLE 3

Cultivation of the *Lactobacillus* Strains

The *Lactobacillus* strains of the invention have been cultivated in a medium consisting of DSM medium 225 (sourdough medium) or mMRS5 (Meroth et al., Appl. Microbiol. Environ. 69:475). The composition contained per liter, 10 g Trypton, 5 g meat extract, 5 g yeast, 10 g maltose, 5 g fructose, 5 g glucose, 5 g Na: acetate×3$H_2O$, 3 g $NH_4Cl$, 2.6 g $K_2HPO_4$×3 $H_2O$, 4 g $KH_2PO_4$, 0.1 g $MgSO_4$×7 $H_2O$, 0.05 g $MnSO_4$×4 $H_2O$, 0.5 g cysteine-HCl, 1 ml Tween 80, 1 ml vitamin mix with cobalamin, folic acid, nicotinic acid amide, pyridoxalphosphate and thiamine (each 0.2 g/L). The sugars were separately autoclaved; the vitamin mix was sterilised by filtration and added after autoclaving. The medium had been sterilised for twenty minutes at 120° C. The pH after sterilisation was preferably 5.8. The gas atmosphere contained 4% $O_2$, about 5% $CO_2$, and balance nitrogen. The breading temperature was 30° C. and the breading duration 24-72 hours. A pure culture was used for inoculation.

EXAMPLE 4

1. Bacterial Culture

*Lactobacillus sanfranciscensis* strains (DSM 23090, DSM 23091, DSM 23092, DSM 23093, DSM 23174, DSM 23200 and DSM 23201) according to the invention, *Lactobacillus rossiae* strain DSM 26024 according to the invention and *Lactobacillus sanfranciscensis* type strain DSM 20451 (DSM GmbH, Braunschweig, Germany), were grown at 30° C. in MRS broth (pH 5.4) containing freshly added 0.15% L-cystein under anaerobic conditions using Anaerogen packages (Anaerogen, Basingstoke, Oxoid, UK) for 24 hours, after inoculation with $0.25 \times 10^7$ of bacteria/mL.

2. Metabolite Analysis

MRS growth media of lactic acid bacteria was subjected to LC-MS/MS analysis for metabolite quantification. The MRS media was filtered with 10 kDa Vivaspin 500 filters (Sartorius Stedim biotech, Goettingen, Germany) before analysis.

Samples were Measured Using:

Dionex Ultra High Performance Liquid Chromatography UltiMate® 3000 (Dionex, Idstein, Germany)
  Pump—HPG-34005D
  Degasser—SRD-3400
  Autosampler—WPS-3000TSL
  Column oven—TCC-3000SD
API 4000 QTRAP, Linear Ion Trap Quadrupole Mass Spectrometer (AB Sciex, Darmstadt, Germany):
  Ionization type—electrospray ionization (ESI)
  Instrument control—Analyst software (AbSciex, Darmstadt, Germany)
  Stationary phase: TSKgel Amide-80 3 μm (150×2 mm, Tosoh Bioscience, Stuttgart, Germany)
  Stationary phase temperature: 40° C.
  Mobile phase:

| eluent A: | acetonitrile/5 mM/L ammonium acetate in water (95 + 5) | | |
|---|---|---|---|
| eluent B: | 5 mM/L ammonium acetate in water (95 + 5) | | |
| gradient: | 0 min | 90% A | 10% B |
| | 5 min | 90% A | 10% B |
| | 10 min | 80% A | 20% B |
| | 15 min | 50% A | 50% B |
| | 18 min | 0% A | 100% B |
| | 21 min | 0% A | 100% B |
| | 24 min | 90% A | 10% B |
| | 30 min | 90% A | 10% B |
| flow: | 200 μl/min | | |

The chromatograms were analysed with Multiquant 2.0 (AB Sciex, Darmstadt, Germany) and concentrations in the samples were calculated according to the spectra of standards.

3. Statistical Analysis

Data are expressed as mean values±standard deviation (SD). All statistical computations were performed using Statistical programming platform R comparing treatment vs. corresponding control group were analyzed using unpaired t-tests. Data comparing several treatments vs. corresponding control group were analyzed using One-Way ANOVA followed by an appropriate multiple comparison procedure. If data was not normally distributed or comprised discontinuous data, non-parametrical tests (Mann-Whitney/Rank sum test, ANOVA on ranks) were used. Differences were considered significant if p-values were <0.05 (*) or <0.01 (**). Principal component analysis (PCA) is described in Pearson, K.; On Lines and Planes of Closest Fit to Systems of Points in Space, Philosophical Magazine (1901), 2 (11), 559-572 and Theodoridis, G., Gika, H. G., Wilson, I. D.; LC-MS-based methodology for global metabolite profiling in metabonomics/metabolomics, TrAC Trends in Analytical Chemistry (2008), 27 (3), 251-260.

4. Results 4.1 LC-MS/MS Analysis of Metabolites in Growth Media of Sourdough Lactic-Acid Bacteria

*Lactobacillus sanfranfranciscensis* strains (DSM 23090, DSM 23091, DSM 23092, DSM 23093, DSM 23174, DSM 23200 and DSM 23210), *Lactobacillus rossiae* strain (DSM 26024) according to the invention and comparative strain, *Lactobacillus sanfranciscensis*-type strain (DSM 20451), were grown for 24 hours in MRS media. The growth media was collected, filtered and analysed using LC-MS/MS.

Figure 2:
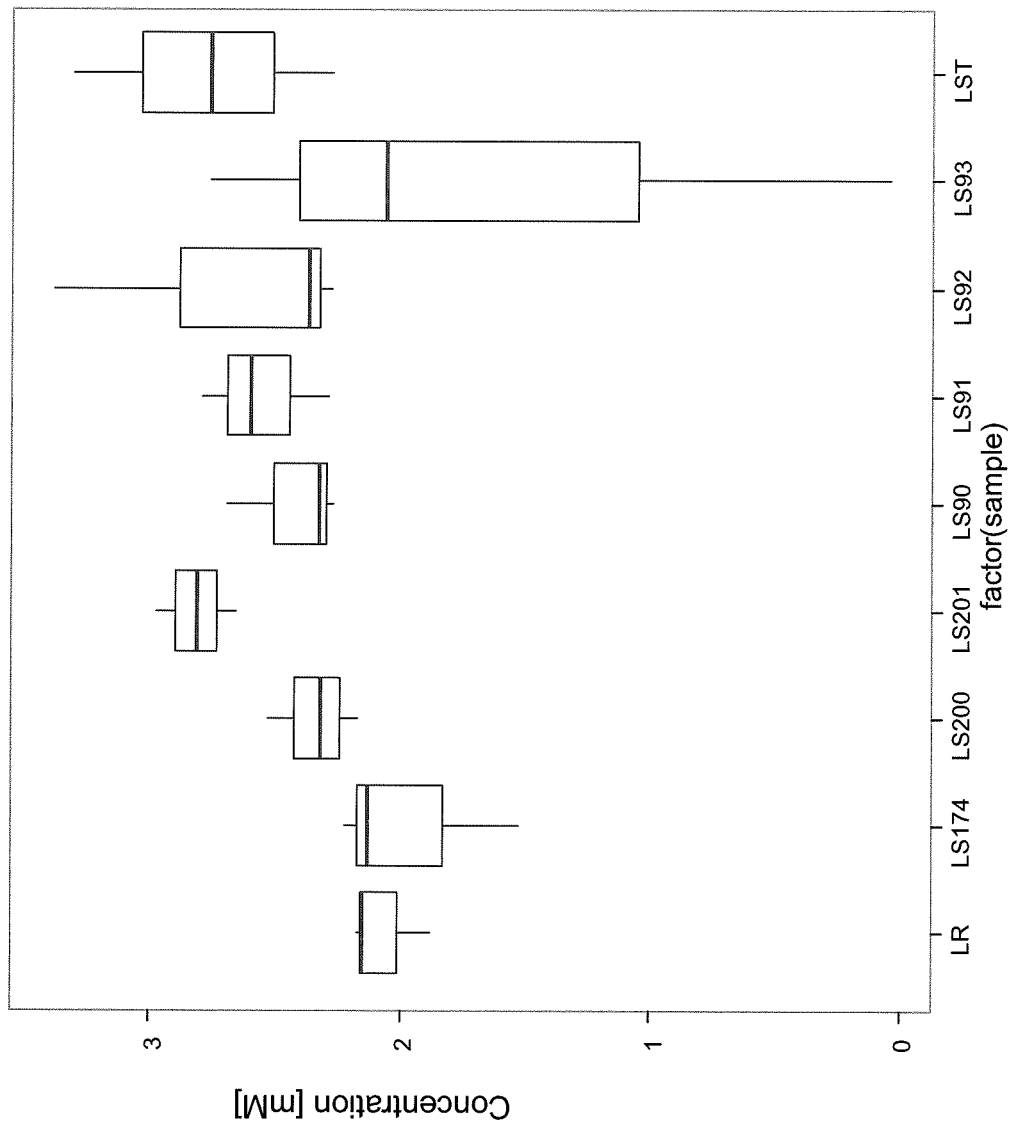
FIG. 2: Amino acid concentrations in MRS media upon 24 hours inoculation with $0.25 \times 10^7$ of lactic acid bacteria/mL of *Lactobacillus rossiae* DSM 26024 (LR), *Lactobacillus sanfranciscensis* strain DSM 23090 (90 LS), *Lactobacillus sanfranciscensis* strain DSM 23091 (91 LS), *Lactobacillus sanfranciscensis* strain DSM 23092 (92 LS), *Lactobacillus sanfranciscensis* strain DSM 23093 (93 LS), *Lactobacillus sanfranciscensis* strain DSM 23174 (174 LS), *Lactobacillus sanfranciscensis* strain DSM 23200 (200 LS), *Lactobacillus sanfranciscensis* strain DSM 23201 (201 LS) and *Lactobacillus sanfranciscensis* type strain DSM 20451 (LST). A: Arginine concentration. B: phenylalanine concentration. C: valine concentration. D: leucine concentration. E: isoleucine concentration. F: histidine concentration.
Figure 2:
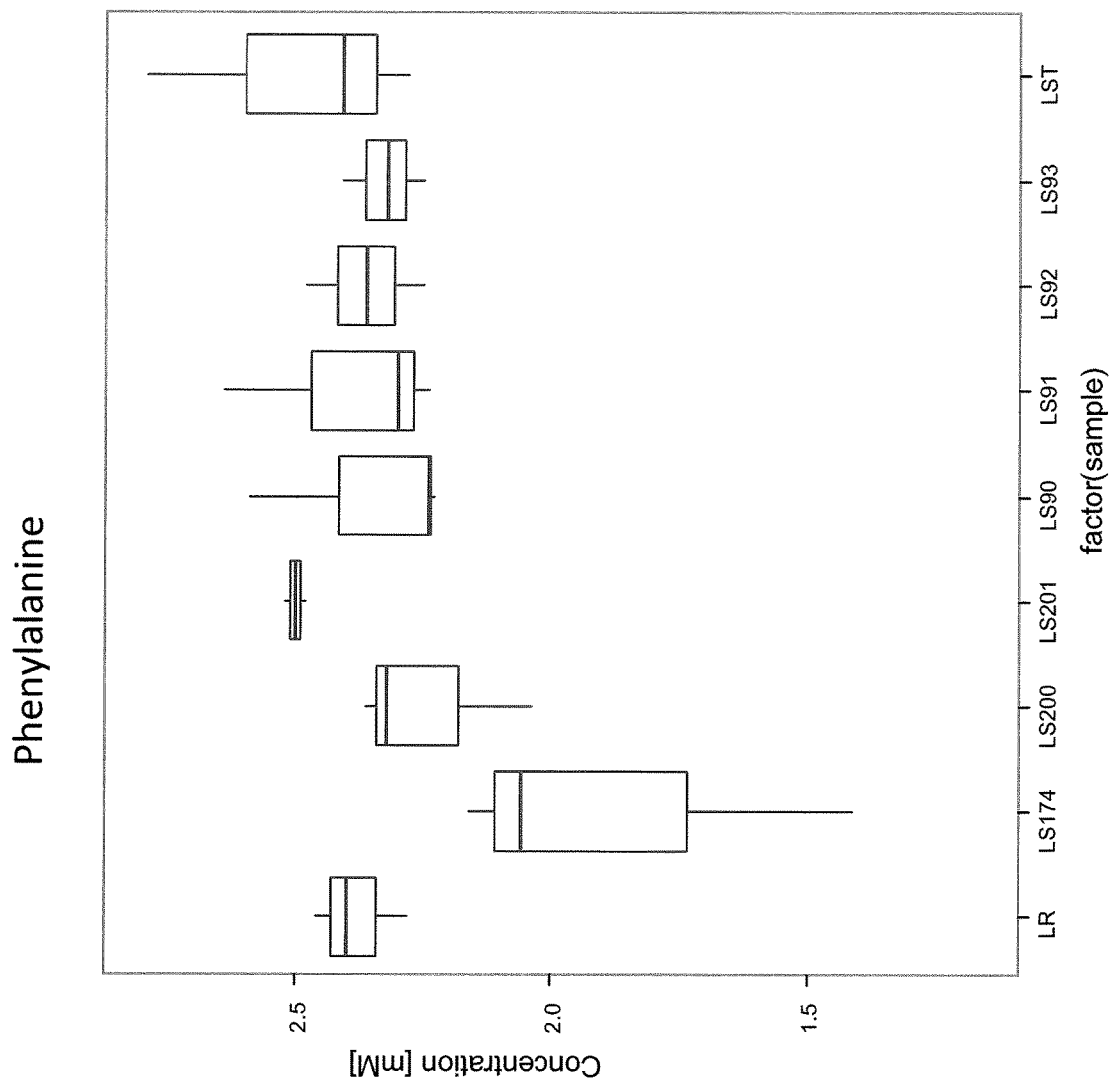
Figure 2:
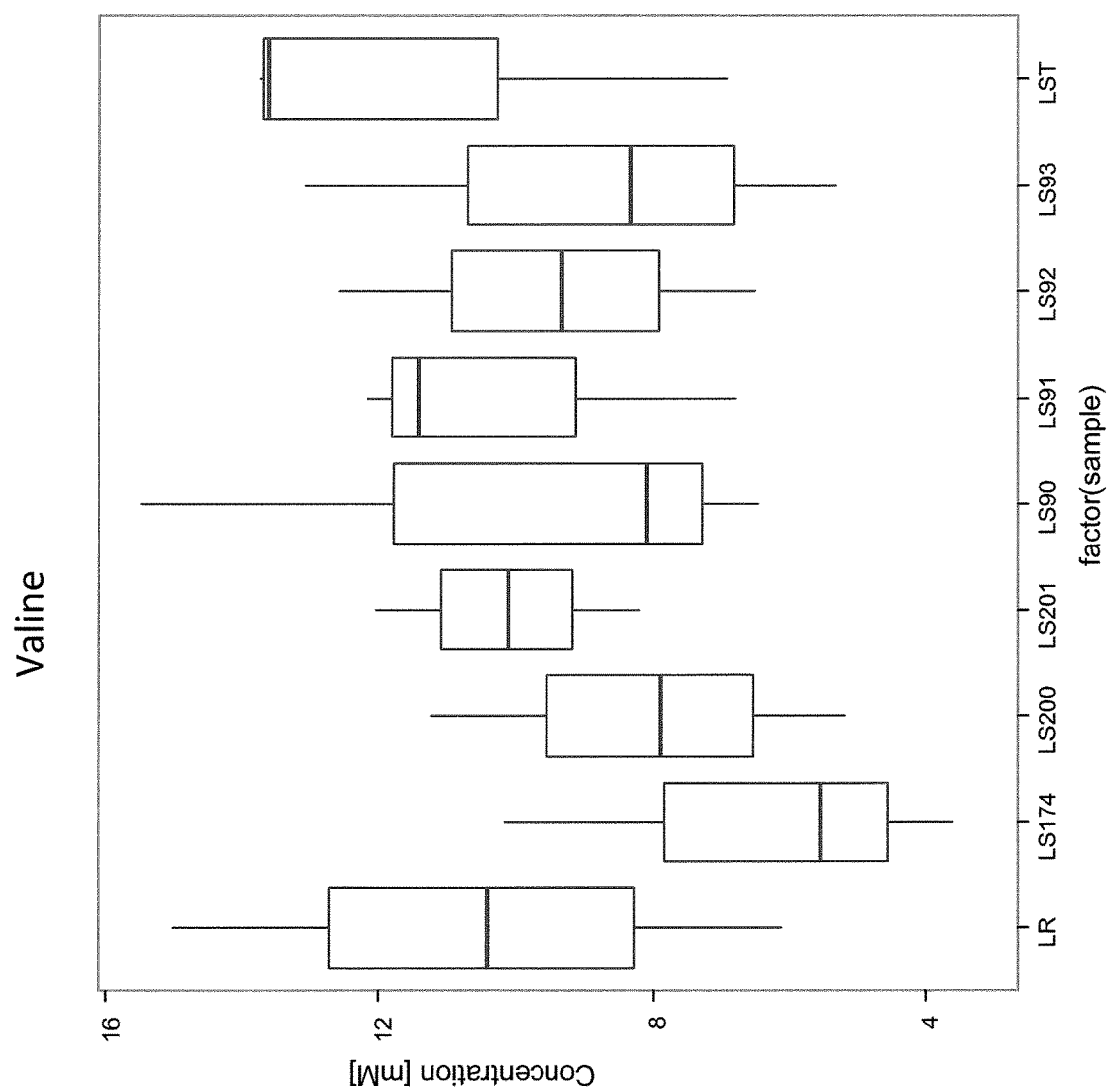
Figure 2:
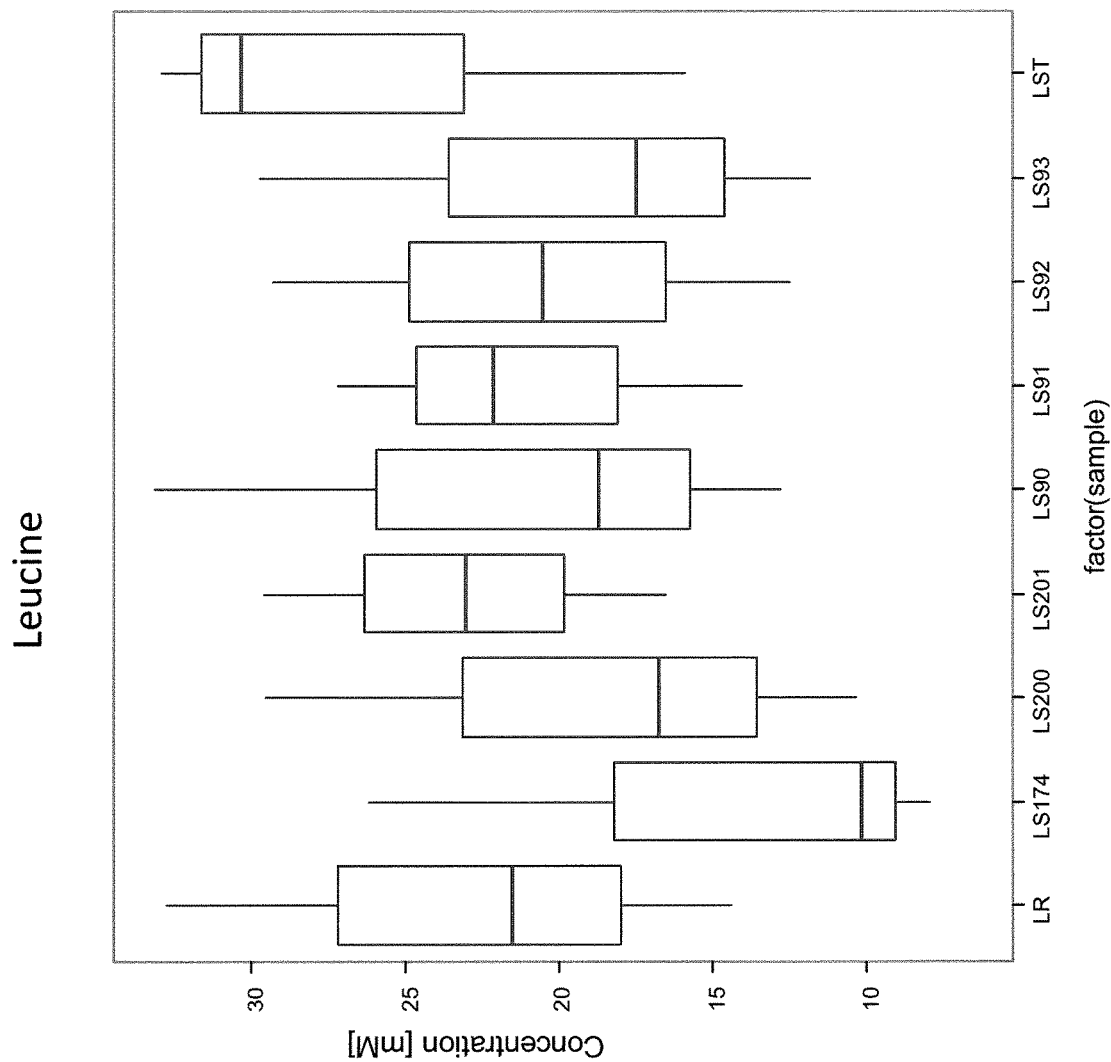
Figure 2:
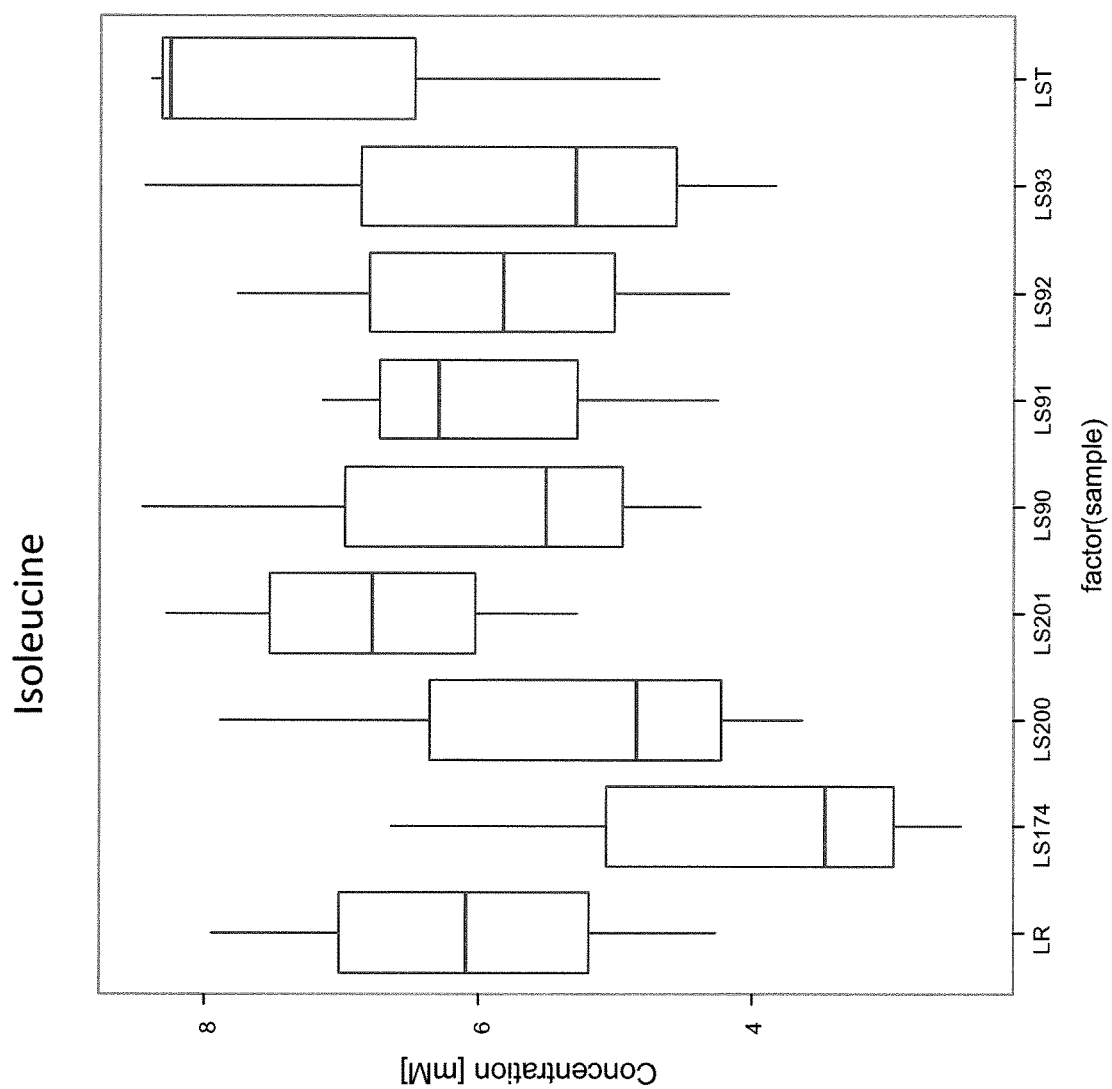
Figure 2:
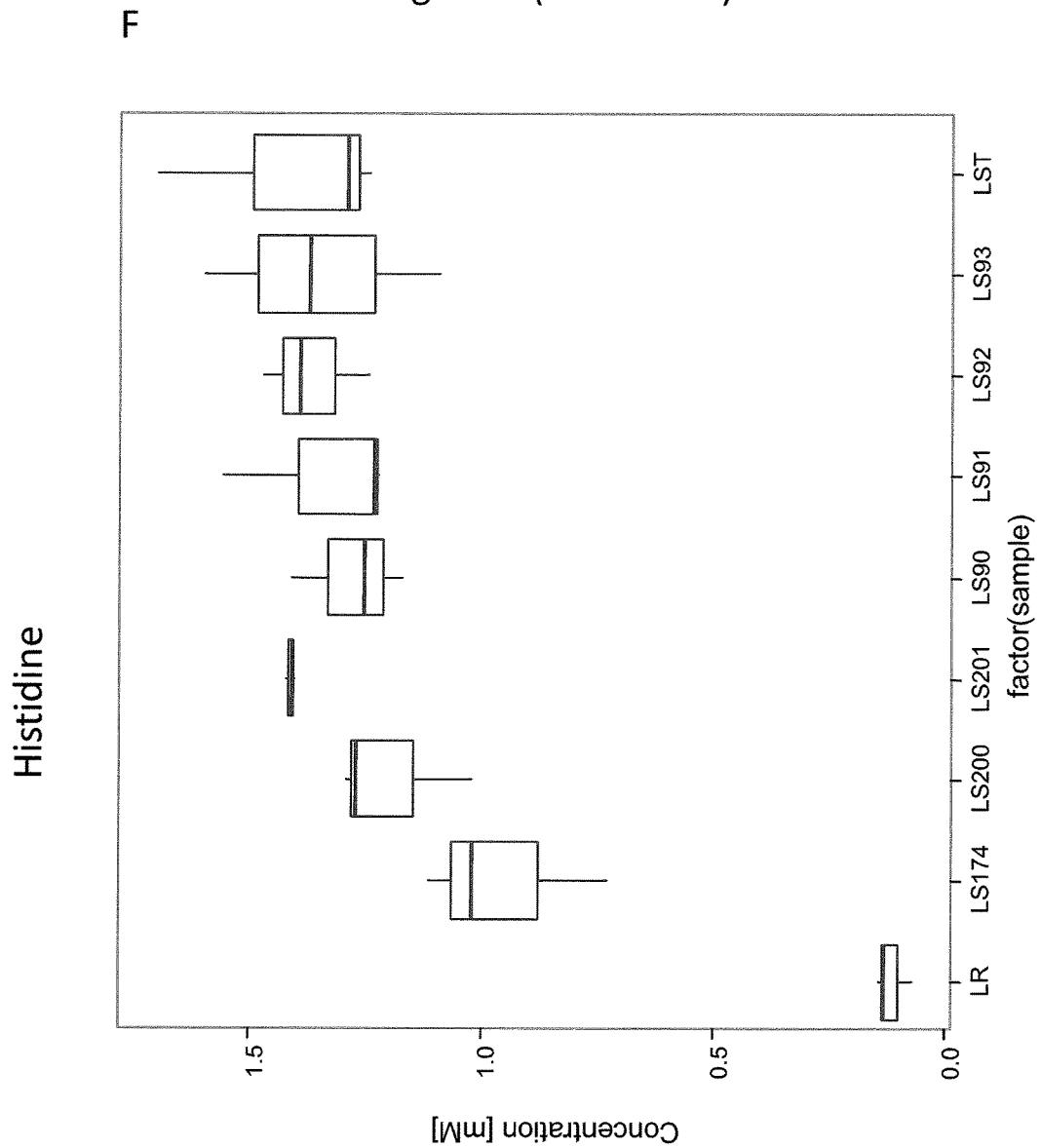

The LC-MS/MS analysis shows significant differences in the metabolite profiles of the *Lactobacillus sanfranciscensis* strains of the present invention compared to *Lactobacillus sanfranciscensis*-type strain (FIG. 1). The amino acids valine, leucine and isoleucine are produced by the lactic acid bacteria of the present invention in significantly lower concentrations than by the *Lactobacillus sanfranciscensis*-type strain (FIG. 2c-e). The concentrations of arginine and phenylalanine are in general slightly lower, the concentration of histidine is, depending on the strain, higher or lower than for the *Lactobacillus sanfranciscensis*-type strain (FIGS. 2a and b as well as 2f). The overall concentration profile of amino acids of the *Lactobacillus sanfranciscensis* strains according to the invention is significantly lower as compared with the one of the *Lactobacillus sanfranciscensis* type strain. Such an amino acid profile is desirable and beneficial for bread production. In particular a low concentration of the amino acids leucine, isoleucine and valine is necessary to reduce the amount of bitter compounds formed during the bread baking process. Thus less salt (NaCl) has to be added to the dough which reduces, among other things, the bitter taste of the dough.

Figure 3:
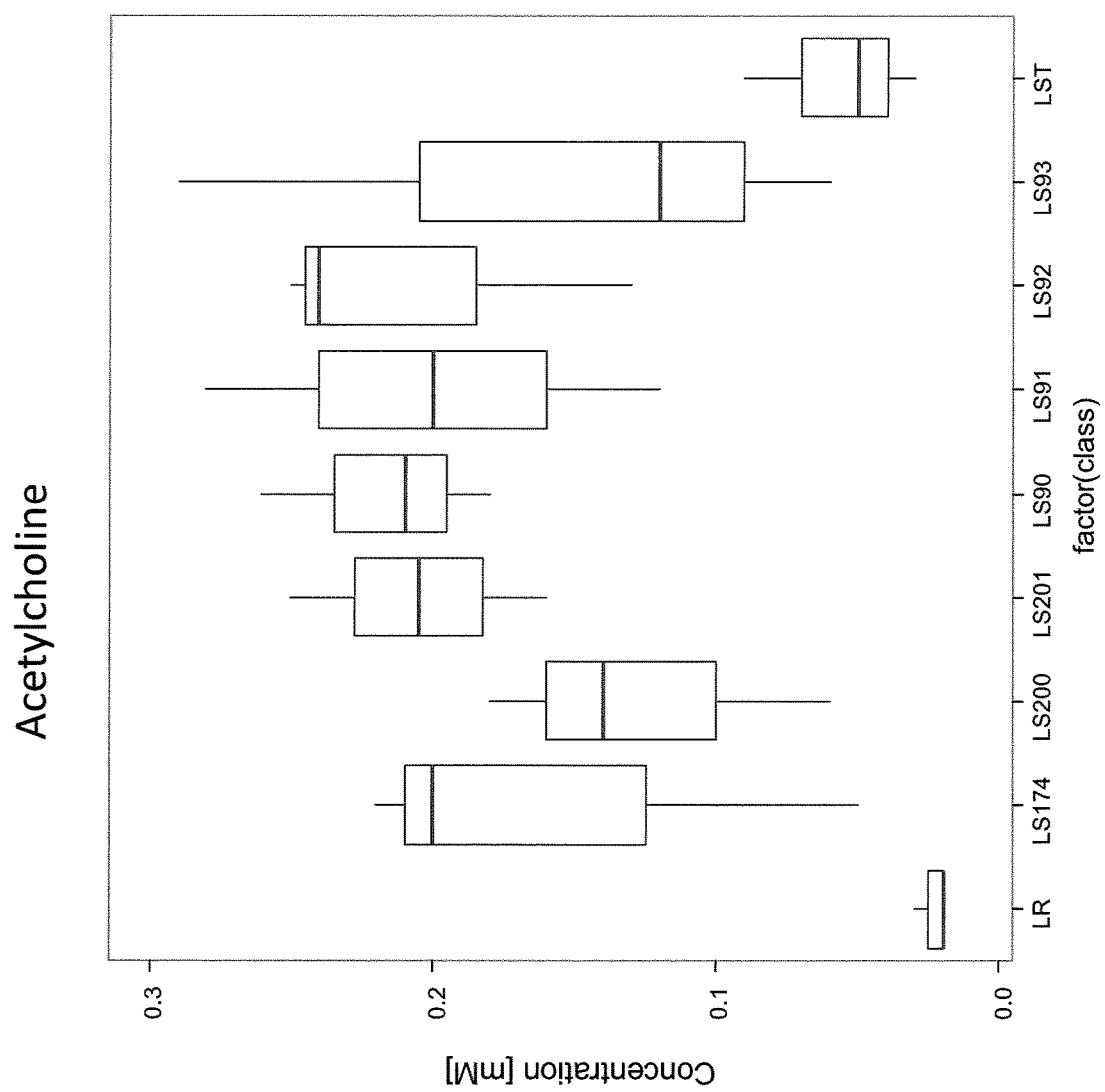
FIG. 3: Acetylcholine concentration in MRS media upon 24 hours inoculation with $0.25 \times 10^7$ of lactic acid bacteria/mL of *Lactobacillus rossiae* DSM 26024 (LR), *Lactobacillus sanfranciscensis* strain DSM 23090 (90 LS), *Lactobacillus sanfranciscensis* strain DSM 23091 (91 LS), *Lactobacillus sanfranciscensis* strain DSM 23092 (92 LS), *Lactobacillus sanfranciscensis* strain DSM 23093 (93 LS), *Lactobacillus sanfranciscensis* strain DSM 23174 (174 LS), *Lactobacillus sanfranciscensis* strain DSM 23200 (200 LS), *Lactobacillus sanfranciscensis* strain DSM 23201 (201 LS) and *Lactobacillus sanfranciscensis* type strain DSM 20451 (LST).

4.2 LC-MS/MS Analysis Revealed the Presence of Acetylcholine in Growth Media of Sourdough Lactic Acid Bacteria FIG. 3 shows a significant difference in the concentrations of produced acetylcholine by various lactic acid bacteria. The highest ACH producer over 24 hours is *Lactobacillus sanfranciscensis* strain DSM 23092. All *Lactobacillus sanfranciscensis* strains of the present invention produce much higher amounts of acetylcholine compared to *Lactobacillus sanfranciscensis*-type strain.

The presence of acetylcholine leads to improved pharmaceutical properties (cf. co-pending application EP 13 153 996.7).

EXAMPLE 5

1. Analysis of the Immune Modulating Properties of Various Bread Types and Sourdough Containing the Bacterial Strains of the Invention Sourdough bread (#1), comparison breads a (#2) and b (#3) as well as sourdough (T) were analyzed. Sourdough bread (#1) was made from sourdough (T) containing the lactic acid bacteria of the present invention.

1.1 Sample Preparation

The samples were portioned, deep frozen (−20° C.) and then freeze-dried. Lyophilized samples were finely ground using a planetary mill and combined to form four mixed samples (1, 2, 3 and T).

Extraction of Active Ingredients from the Samples

To simulate conditions in a human stomach, the active ingredients have been extracted by taking up 1 g of powder of the various samples (several repetitions) in 10 ml HCl (150 mM; pH 2) followed by incubation over 2.5 hours at 37° C. using an overhead rotator placed in an incubator.

Then the samples were processed as follows:

a) Suspension

To produce a suspension (powder with HCl) the incubated samples were combined and the pH value was adjusted to 7 with 8.25 M NaOH. The samples were portioned and freeze-dried at −70° C.

b) Supernatant

To produce a supernatant the suspension was centrifuged over 10 minutes at a rate of 4,000 r/min. The resulting supernatant was removed above the residue (pellet), then samples were combined and the pH value adjusted to 7 as described under a). After that, the samples were portioned and freeze-dried.

c) Pellet

To produce a pellet the residue from (b) was washed twice using 10 ml of 0.9% NaCl solution so as to completely remove the extraction agent from the sample. Then the pellet was coated with 10 ml of 0.9% NaCl solution and frozen in a "wet" condition.

1.2 Whole Blood System

The analysis of immune modulating or HOCl detoxifying properties was performed using a whole blood test system. Whole blood from three healthy human donors was utilized. During the reaction of activated immune cells, reactive oxygen species (ROS) are released, among others HOCl=hypochlorous acid. This leads to the pathogen being killed. Using a selective indicator (ACC; 1-aminocyclopropane-1-carboxylic acid) for the production of HOCl (hypochlorous acid) this effect was measured by means of gas chromatography. The pellet, the suspension as well as the supernatant of samples 1, 2, 3 and T were analyzed in a whole blood system using blood from three donors.

1.2.1 Detoxification of ACC Cleavage Using Hypochlorous Acid (HOCl)

This method allows to understand whether the test substances used are capable of reacting with HOCl. If so, the anti-oxidative effect identified in a whole blood system could be assigned at least partially to a reaction with HOCl. HOCl was thus rendered harmless for other reactions ("detoxified").

Figure 4:
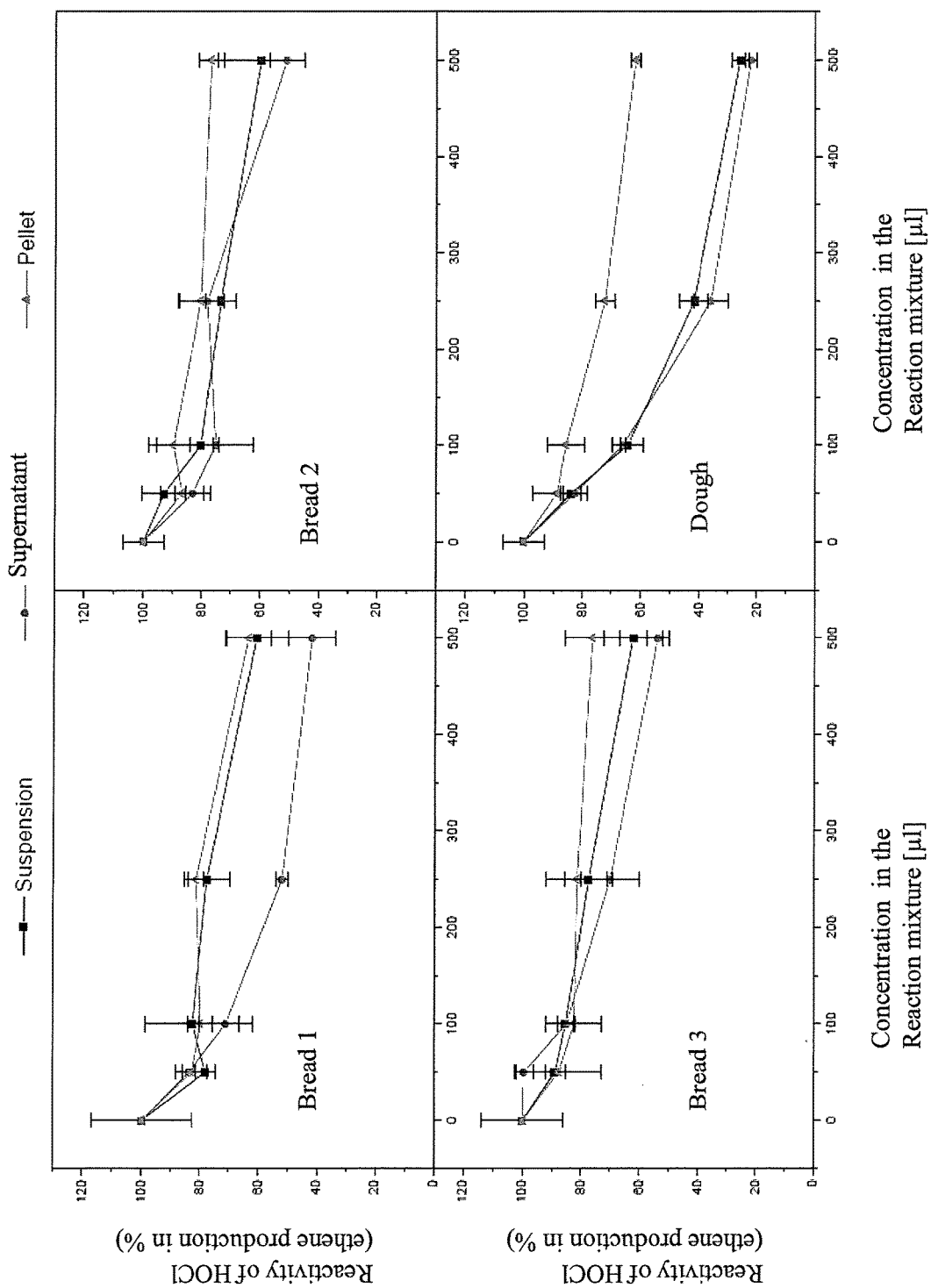
FIG. 4: Effect of various bread and dough samples onto HOCl detoxification.

FIG. 4 shows that the sourdough inhibited the ACC cleavage significantly better than the bread samples. Suspension and supernatant displayed the same reactivity with HOCl. Active water-soluble components were found in the supernatant. All bread types only showed a limited detoxification effect regarding HOCl. There were no clear differences between the various fractions. It seems that the baking process leads to the activity of water-soluble components getting lost.

1.2.2 Whole Blood System with Zymosan as an Activator

In this case, the immune cells in the whole blood were stimulated using zymosan (cell wall component of yeast) so that various reactive oxygen species were produced. This led among other things to HOCl being released which reacted with ACC to produce ethylene. The ethylene quantity produced was a measure of the activity of immune cells. The less ethylene was contained in a sample the less immune cell activity was observed.

Figure 5:
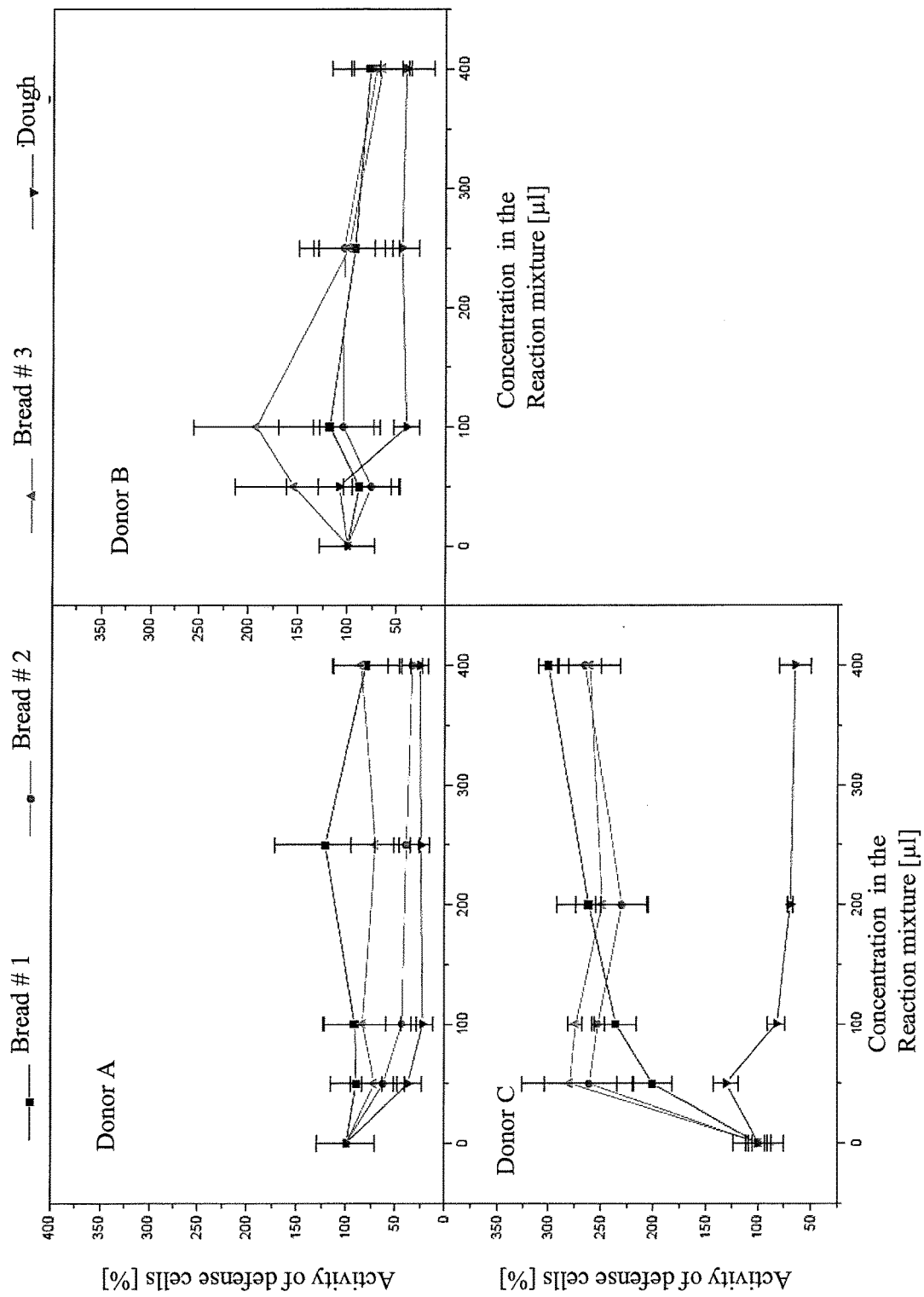
FIG. 5: Effect of various bread and dough samples in a whole blood system with zymosan.

FIG. 5 shows that the sourdough displays best anti-oxidative effects as well as the highest anti-oxidative potential and the reaction was inhibited in all donors. Bread #2 reduced immune cell activity only in donor A whereas bread #2 had no impact on donor B. For donor C, the reaction was stimulated across all bread types. Bread #1 and #3 had no impact on the reaction in the blood of donor A, and bread #3 induced a stimulation in donor B at the beginning but had no influence on the reaction in higher concentrations. This can be explained by the baking process where substances acting as antioxidants got lost.

1.2.3 Whole Blood System without Zymosan as an Activator

In this case no zymosan was added to the reaction sample. If the test substances used nevertheless showed an effect in the system, i.e., if ethylene was produced, the immune cells were stimulated by the test substance. This way, an immune modulating or immune stimulating effect could be detected.

Figure 6:
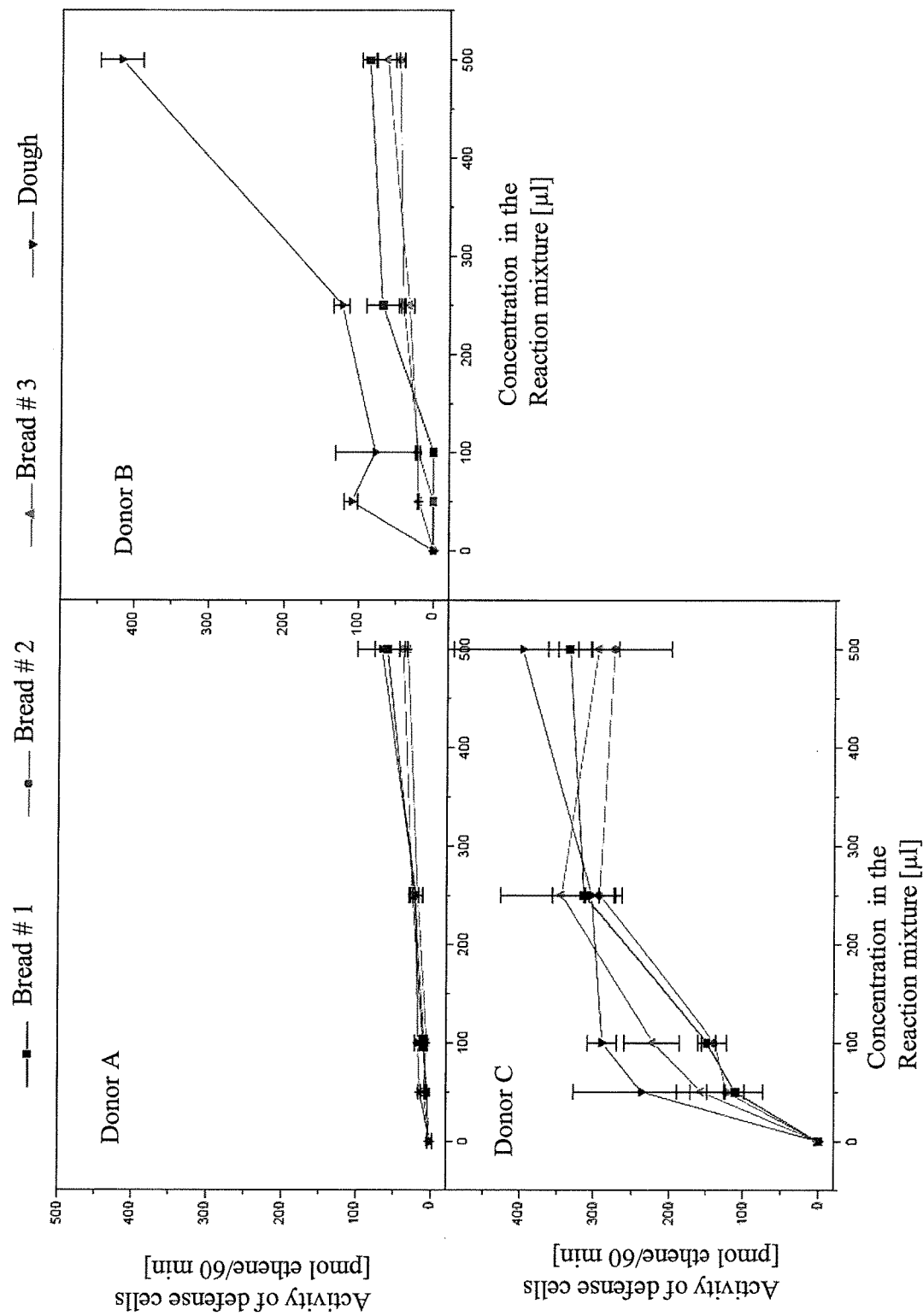
FIG. 6: Effect of various bread and dough samples in a whole blood system without zymosan.

FIG. 6 shows that the immune cells of all donors could be stimulated by the various samples. The effect was strongest for donor C and for the sourdough sample in donor B. Except for donor B no clear differences could be observed between sourdough and bread which means that immune stimulating properties did not get lost during the baking process. The stimulating effect of sourdough bread #1 tended to be higher than that of comparison breads and the difference was strongest in donor A.

Generally it can be stated that the effect of the suspension was always strongest and that the effect of the pellet and the supernatant was at a comparable level. Thus there is a synergistic effect of water-soluble components in the supernatant in combination with the pellet ingredients.

The pellet was more stimulating in lower concentrations and the activation potential decreased as the concentration was increased. This suggests that the stimulation depends on the receptor and that the components of samples intervene in the signal transduction process respectively.

The invention claimed is:

1. A composition comprising at least one *Lactobacillus* strain selected from the group consisting of strains DSM 23090, DSM 23091, DSM 23200, DSM 23092, DSM 23093, DSM 23201, DSM 23174, DSM 23121 and DSM 26024 wherein said composition is in a form of a coated tablet and wherein the composition contains the *Lactobacillus* strain in an amount of $10^7$ to about $10^{12}$ cfu/g based on the total weight of the composition.

2. The composition according to claim 1 wherein the composition comprises a single *Lactobacillus* strain.

3. The composition according to claim 1, comprising at least one further microorganism.

4. The composition according to claim 1, wherein the at least one further microorganism is a bacterium and/or yeast, selected from the group consisting of a *Lactobacillus sanfranciscensis* strain, *Lactobacillus rossiae* strain, *Lactobacillus plantarum* strain, *Lactobacillus brevis* strain, *Lactobacillus amyolyticus* strain, *Lactobacillus amylovarus* strain, *Lactobacillus delbruckii* strain, *Lactobacillus pontis* strain, *Lactobacillus acidophilus* strain, *Lactobacillus lactis* strain *Gluconobacter oxydans* strain, *Candida humilis* strain, *Candida milleri* strain, *Candida krusei* strain, *Saccharomyces exiguus* strain, *Saccharomyces barnetti* strain, *Saccharomyces cerevisiae* strain and *Saccharomyces minor* strain.

5. The composition according to claim 1, further comprising an excipient and/or carrier selected from the group consisting of natural mineral flour, synthetic mineral flour, adjuvants and/or dispersing agents.

6. The composition according to claim 1, wherein said natural mineral flour is kaolin or talc, said synthetic mineral flour is a silicate, said adjuvant is glycol and/or said dispersing agents is methyl cellulose.

7. The composition according to claim 1, further comprising a non-digestible oligosaccharide.

8. The composition according to claim 7, wherein said non-digestible oligosaccharide is selected from the group consisting of fructo-oligosaccharides, galacto-oligosaccharides, lactolose, xylo-oligosaccharides, ismalto-oligosaccharides, soy bean oligosaccharides, gentio-oligosaccharides, gluco-oligosaccharides, fructans, lactosucrose, short-chain fructo-oligosaccharides, and mixtures thereof.

9. The composition according to claim 1, further comprising a carrier selected from the group consisting of natural and synthetic mineral flours, silicon dioxide and diatomaceous earth.

10. The composition according to claim 1, wherein the composition comprises a mixture of at least two *Lactobacillus* strains.

11. The composition according to claim 1, wherein the *Lactobacillus* strain is DSM 23090.

12. The composition according to claim 1, wherein the composition contains the *Lactobacillus* strain in an amount of about $10^7$ to about $10^{12}$ cfu/g based on the total weight of the composition.

13. The composition according to claim 1, wherein the composition contains the *Lactobacillus* strain in an amount of about 0.1 to about 99% by weight based on the total weight of the composition.

14. A composition comprising a *Lactobacillus* strain according to claim 1 further comprising a carrier suitable for human or veterinary medicine or a carrier suitable for cosmetic compositions.

15. A method for modulating an immune response comprising administering a composition according to claim 14 to a subject in need of such treatment.

16. A method for the manufacture of human food products and food supplement products or animal feed products comprising adding the composition according to claim 1 to said human food products and food supplement products or animal feed products.

17. The method according to claim 16, wherein the food product, food supplement product or feed product is a fermented product.

18. The method according to claim 16, wherein the food product is a sourdough or a beverage.

19. The method according to claim 18, wherein the sourdough is sourdough for use in bread.

20. A method for improving food products, comprising adding the composition according to claim 1 to a food product.

21. The method according to claim 20, wherein said food product is oat flakes or yoghurt.

22. The method according to claim 20, wherein said food product is a fermented product.

23. The method according to claim 22, wherein said fermented product is selected from the group consisting of bread dough, yoghurt, cheese, alcoholic and non-alcoholic beverages, kimchi, fermented seafood, soybean paste, and wort.

24. A fermentation starter comprising the composition according to claim 1, on a carrier selected from the group consisting of silicon dioxide and diatomaceous earth.

25. A food supplement comprising the composition according to claim 1 in combination with p-glucans or polyphenols.

* * * * *